US009804182B2

(12) United States Patent
Nuotio et al.

(10) Patent No.: US 9,804,182 B2
(45) Date of Patent: Oct. 31, 2017

(54) HANDLING PACKAGE OF CUVETTES

(75) Inventors: Vesa Nuotio, Vantaa (FI); Juhani Makunen, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 130 days.

(21) Appl. No.: 13/522,136

(22) PCT Filed: Feb. 22, 2011

(86) PCT No.: PCT/FI2011/050162
§ 371 (c)(1),
(2), (4) Date: Jul. 13, 2012

(87) PCT Pub. No.: WO2011/104438
PCT Pub. Date: Sep. 1, 2011

(65) Prior Publication Data
US 2012/0292220 A1  Nov. 22, 2012

(30) Foreign Application Priority Data

Feb. 26, 2010  (FI) ...................................... 20105191

(51) Int. Cl.
*B65D 85/00* (2006.01)
*G01N 35/02* (2006.01)

(52) U.S. Cl.
CPC .................. *G01N 35/026* (2013.01)

(58) Field of Classification Search
CPC .... B65D 5/0227; B65D 21/0201; B65D 1/34; B65D 25/04; B65D 71/0014; G01N 35/026; G01N 2035/023; G01N 2035/0401; B01L 3/502
USPC ....... 206/526, 504, 338, 345, 558, 560, 340, 206/528, 538, 460, 820, 569; 220/23.83, 220/592.02, 507, 23.2, 23.4, 23.8; 249/121; 422/552, 554
See application file for complete search history.

(56) References Cited

U.S. PATENT DOCUMENTS

| 2,027,754 A | * | 1/1936 | Smith ........................... 249/134 |
| 2,428,056 A | * | 9/1947 | Wachsman .................... 220/719 |
| 2,981,039 A | * | 4/1961 | Pohl ................................ 53/457 |

(Continued)

FOREIGN PATENT DOCUMENTS

| CN | 1637418 A | 7/2005 |
| CN | 1826223 A | 8/2006 |

(Continued)

*Primary Examiner* — J. Gregory Pickett
*Assistant Examiner* — Rafael Ortiz
(74) *Attorney, Agent, or Firm* — Seppo Laine Oy; Toimi Teelahti

(57) ABSTRACT

Automatic analyzers, in which the liquids to be analyzed are in so-called reaction vessels, simultaneously acting as optically high-quality cuvettes (10), are used in laboratories for analyzing various liquids. Further described is a handling package for cuvettes (10). A removable bonding strip (100) is fastened on the rows of cuvettes (10), the strip (100) binding the rows of cuvettes (10) during transport, and being easily removable when the cuvettes (10) are loaded into the instrument. The cuvettes (10) are loaded into the instrument by supporting the package in its place from the brackets (24) located in the ends of the cuvettes (10), so that the strip (100) can be pulled off the supported package of cuvettes (10).

18 Claims, 2 Drawing Sheets

(56) References Cited

U.S. PATENT DOCUMENTS

| | | | | |
|---|---|---|---|---|
| 3,759,374 | A * | 9/1973 | Helger et al. | 206/431 |
| 4,251,159 | A * | 2/1981 | White | G01N 21/03 356/246 |
| 4,599,314 | A * | 7/1986 | Shami | 435/305.3 |
| 4,608,231 | A * | 8/1986 | Witty | B01L 3/502 206/569 |
| 4,690,900 | A | 9/1987 | Kimmo et al. | |
| 4,877,659 | A * | 10/1989 | Vince | B01L 3/5085 206/558 |
| 4,889,254 | A * | 12/1989 | Vola | 220/23.4 |
| 5,071,001 | A * | 12/1991 | Ryman, III | 206/139 |
| 5,110,556 | A * | 5/1992 | Lyman et al. | 422/552 |
| 5,308,584 | A * | 5/1994 | Vauramo | 422/566 |
| 5,514,343 | A * | 5/1996 | Verwohlt | B01L 3/5085 211/74 |
| 5,670,118 | A * | 9/1997 | Sponholtz | B01L 3/5085 422/119 |
| 5,948,363 | A * | 9/1999 | Gaillard | B01L 3/5085 422/552 |
| 6,328,164 | B1 * | 12/2001 | Riekkinen | B01L 3/5085 206/460 |
| 2002/0027093 | A1 | 3/2002 | Riekkinen et al. | |
| 2005/0218031 | A1 * | 10/2005 | Murphy | 206/538 |
| 2008/0031776 | A1 * | 2/2008 | Sevigny et al. | 422/64 |
| 2008/0088835 | A1 | 4/2008 | Freeman, III et al. | |
| 2008/0245800 | A1 * | 10/2008 | Moore | 220/507 |

FOREIGN PATENT DOCUMENTS

| | | |
|---|---|---|
| JP | 2003-315346 A | 11/2003 |
| WO | WO 03/039230 A2 | 5/2003 |
| WO | WO 2009/024956 A1 | 2/2009 |
| WO | WO 2009/144380 A2 | 12/2009 |

* cited by examiner

HANDLING PACKAGE OF CUVETTES

The present invention relates to a handling package of cuvettes that can be used for loading cuvettes packed in such a package into an instrument, for protecting cuvettes during storage and transport and as a substrate for various markings.

Automatic analyzers, in which the liquids to be analyzed are in so-called reaction vessels, simultaneously acting as optically high-quality cuvettes, are used in laboratories for analyzing various liquids. The row of reaction vessels or a cuvette can generally consist of a number of reaction vessels or positions separated from each other with a wall molded into a row as one piece. The reaction vessels are grouped so that there is a common wall between them and the long sides of the cuvette are straight so that the cuvettes can be placed one after the other as a uniform row so that the long sides of adjacent cuvettes are closely against each other. Thus the cuvettes can be placed in a square box during transport and other handling. Such a cuvette is disclosed in U.S. Pat. No. 4,690,900. Cuvettes of this kind are simple to handle and they can be used for producing reliable measurement results.

Cuvettes must remain dustless, scratchless and intact for the radiation flux, allowed to pass through the measurement surfaces of the reaction vessels in the instrument carrying out the analysis, to provide reliable analysis results. Because of this cuvettes must be handled with great care immediately after the manufacturing phase during packaging, storage, transport and operation.

During use of such cuvettes there has arisen a need to provide a loading method that would guarantee that the cuvettes are absolutely dust-free, scratch-free and without fingerprints when taken into use. The packaging step of cuvettes after injection pressing can be controlled by means of automation methods and apparatuses, but the impacts on the cuvette packages and incorrect handling by humans when loading the cuvettes to the instrument carrying out the analysis have been problematic. A packaging method for cuvettes in which the cuvettes are packaged as a row in a box having a removable lid has been developed to avoid these disadvantages. The opening of the package has been shaped to fit the feed opening of the cuvettes and the lid comprises a pushing means for pushing the cuvettes into the instrument. Cuvettes are transferred to the instrument while the package is fastened to the feed opening of the instrument by pushing the row of cuvettes in the box from behind with the removable lid of the package having a separate pushing means forming other end of the package when the lid is fastened to the package. The advantages of this packaging method are dust-free handling, no fingerprints on the optical area and no scratches caused by manual handling.

Such a box package, however, has its disadvantages that reduce its handling capability and increase packaging costs. The manufacture of the package box is quite expensive in relation to the price of the cuvettes, so the package increases the cost of single analyses. The box produces a lot of plastic waste that has to be transported to the waste disposal site or to plastic waste recycling. As the consumption of cuvettes is very great in many laboratories and the material of the box might not be the same plastic as the other plastic waste of the laboratory, the solution if a bad one for recycling. Separating and storing the packages in the laboratory is difficult. Because the cuvettes are disposable and they should only be recycled as material, the package should comprise as little material as possible and the packaging materials should be easy to collect and recyclable. The cuvettes as such could be washed and reused, but as their optical surfaces are very sensitive to dirt and mechanical damage, the cuvettes are easily damaged during collecting, transport and washing. This is the reason the manufacturers of cuvettes forbid recycling of cuvettes, as the risk of incorrect results due to damaged cuvettes is great when using recycled cuvettes.

Due to cost reasons and to save materials the package box of cuvettes has to be made of a thin material whereby it can't be made very stiff. Therefore it is easily bent and twisted and is to some degree difficult to use and the box and the position of the cuvettes is easily skewed, the cuvettes fall over during insertion and the opening of the box can slip away from the feed opening of the instrument. When fallen or skewed cuvettes are directed or lifted by hand, they easily get fingerprints and even scratches that can lead to incorrect measurement results. A problem with the package is also that the feed apparatuses of different instruments accommodate a different number of cuvettes at a time, whereby some cuvettes always remain in the box and at the next introduction the cuvettes will have to fed from two boxes, whereby the number of misfeeds is always larger.

U.S. Pat. No. 6,328,164 discloses a handling package for cuvettes, the package comprising rows of currently used cuvettes comprising a number of reaction vessels and a bonding strip joining the cuvettes together. Each cuvette includes a hook part for taking a hold of when moving the cuvette in the instrument. The bonding strip is fastened to the cuvettes by means of adhesive substance applied to the lower surface thereof and the strip is fastened to the upper part of the cuvettes on the surface on the side of the openings of the reaction vessels. In this package the bonding strip is slightly narrower than the upper side of the cuvette so that the edges of the cuvettes could be supported by a molding or the like on the edges of the feed apparatus. The cuvettes must be supported by their sides for removing the bonding strip. The solution is inexpensive and reliable, but the fact that the bonding strip does not easily extend well enough over the outermost positions or the openings of the reaction vessel, whereby dust or other impurities can enter the vessel, can be considered as its disadvantage.

The purpose of the present invention is to provide a handling package for cuvettes, the package comprising a novel type of cuvettes and a novel strip for fastening the cuvettes.

The invention is based on the idea of fastening a removable bonding strip on the row of cuvettes, the strip binding the row of cuvettes during transport and being easily removable when the cuvettes are loaded into the instrument. The binding strip must extend at least over the openings of the reaction vessels, preferably at least over the whole width of the top surface of the row of reaction vessels.

Considerable advantages are achieved by means of the invention.

The cuvettes are bound into a package by means of a simple tape or another corresponding strip fastening the rows of cuvettes to itself from the top. Thus, in addition to the cuvettes, the package does not comprise other parts or materials than the easily disposable tape. This means the amount of packaging material to be disposed of is as small as possible. The strip protects the reaction bowls from dust and impurities including the openings of the outermost reaction vessels. The number of cuvettes in one handling package and the size of the instrument loading apparatuses can be standardized.

The cuvettes can be easily loaded into a suitably designed apparatus from a handling package according to the invention and because preferably the whole package of cuvettes is loaded at a time, there is no need or even a possibility to handle the cuvettes as separate parts. This allows ensuring the hygienic and optical cleanness of the cuvettes as well as possible and to avoid their mechanical damage. Dirty and damaged cuvettes essentially reduce the reliability of the produced measurement results, so the cleanness and undamaged state of the cuvettes is essentially important for the reliable operation of the cuvettes. It is especially advantageous that the bonding strip extend over the whole length of the top surface of the cuvettes, whereby it will reliably cover all openings of the positions of the reaction vessels.

In the following, the invention is disclosed in more detail by means of reference to the appended drawings.

Figure 1:
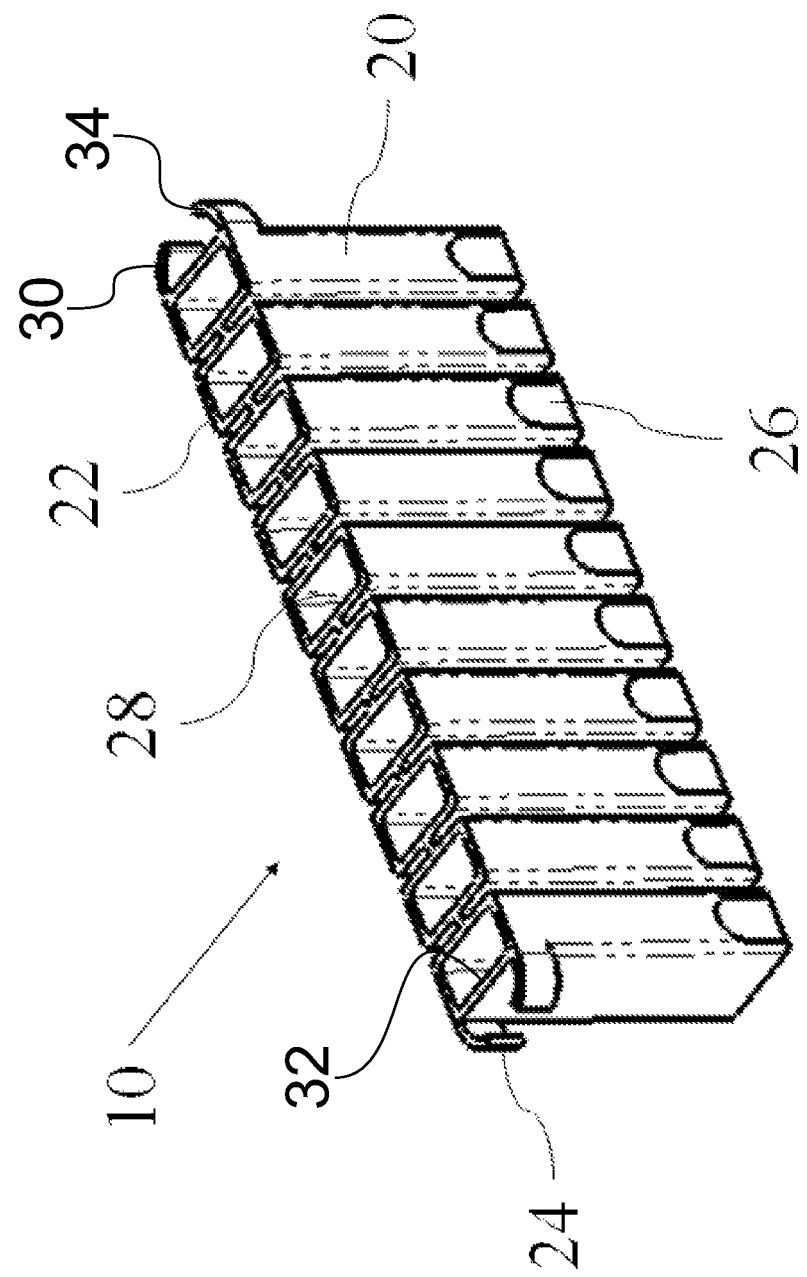
FIG. 1 illustrates one handling package of cuvettes according to the invention.

As can be seen in FIG. 1, the cuvette 10 comprises positions 20, i.e. reaction vessels arranged adjacent each other in a row. Here, the term cuvette 10 means a means for receiving samples having at least one position 20 for receiving the sample and for storing it at least during the analyzing. Position 20 is a tubular vessel inside which a sample volume 28 is defined for the sample to be analyzed. According to one embodiment the shape of the position 20 is a rounded rectangle and generally such that the sides of the opening of the sample volume 28 are considerably shorter than its depth. The sample volume 28 can also be different in shape. In this context the direction of the longest side of the sample volume 28 of the position 20, the depth, is called the vertical axis. Correspondingly, horizontal axis means the cartesian axes in right angles to the vertical axis.

According to one embodiment the cuvette 10 comprises 10 positions separated from each other by intermediate walls 22. The intermediate wall 22 is the isthmus-like connecting part between two positions 20. As can be seen from FIGS. 1 and 2, the intermediate wall 22 is essentially central to the narrow facets of adjacent positions 20 so that the intermediate wall 22 extends from the upper edge of the cuvette 10 to about halfway up the side facet of the positions 20. In other words, the intermediate wall 20 does not connect the positions 20 in their whole length but only in their upper half. The basic idea of the intermediate wall 22 is to be a connecting element that does not advance heat transfer from one position to another, but rather it, on the contrary, isolates the positions 20 from each other. Thus the heat conducted between positions 20 remains as low as possible and the analysis accuracy is improved. In this invention the construction of the intermediate wall is not important, it is sufficient that the positions are somehow connected to each other so that they can be formed into a cuvette having a number of reaction vessels, i.e. positions in a row.

As can be seen in FIG. 1, the outermost positions 20 are provided with brackets 24. According to an embodiment of the invention the bracket 24 comprises two tabs that are essentially shorter than the cuvette 10 in vertical direction of the cuvette 10 and fairly delicate in thickness. The tabs of the bracket 24 extend outwards from the upper part of the outer edge of the outermost positions 20 so that the tabs curve towards each other. The outer edge of the position 20 means the side edge of either of the outermost position 20 not having an intermediate wall 20. Correspondingly, the direction facing outwards is the horizontal direction extending towards the outer edge of the position 20 from the intermediate edge 22. The top surface of the row of reaction vessels means the area between the outer edges of the side walls of the outer positions without intermediate walls. Thus the brackets 24 are not included in the top surface of the row of reaction vessels.

Like the intermediate walls 22, the brackets 24 can be made of elastic material, due to which they can also resiliently withstand bending of their longest side. The bending properties of the brackets 24 are needed in some embodiments of the cuvette. Within this invention, the shape and location of the brackets can vary from what is described above. According to the invention it is important that the brackets are located on both sides of the row of reaction vessels and that they comprise a guiding top surface 30 that can be supported against the limiter surface. The guiding top surface 30 can be in a different level than the top surface of the row of reaction vessels, being located either on the outer side of the outermost positions or being slightly higher than the surface of the row of reaction vessels. The shape of the brackets can be freely chosen and arranging the brackets on different locations forms an identification system in which only cuvettes having correctly arranged brackets with correct shape fit a feed apparatus. This can be useful when a certain analyzer may be fed only certain samples due to e.g. risk of contamination. This allows forming a key/lock pair from the cuvettes and the feed apparatus, the pair preventing incorrect samples from entering the analyzer. The feed apparatus can correspondingly be provided with a counter apparatus whereby e.g. differently coded cuvettes are used for different customers of the laboratory and the amount of performed tests can be verified from the reading of the feed apparatus. This method of verifying can be used as a support and control means for other sample monitoring of the apparatus.

Figure 2:
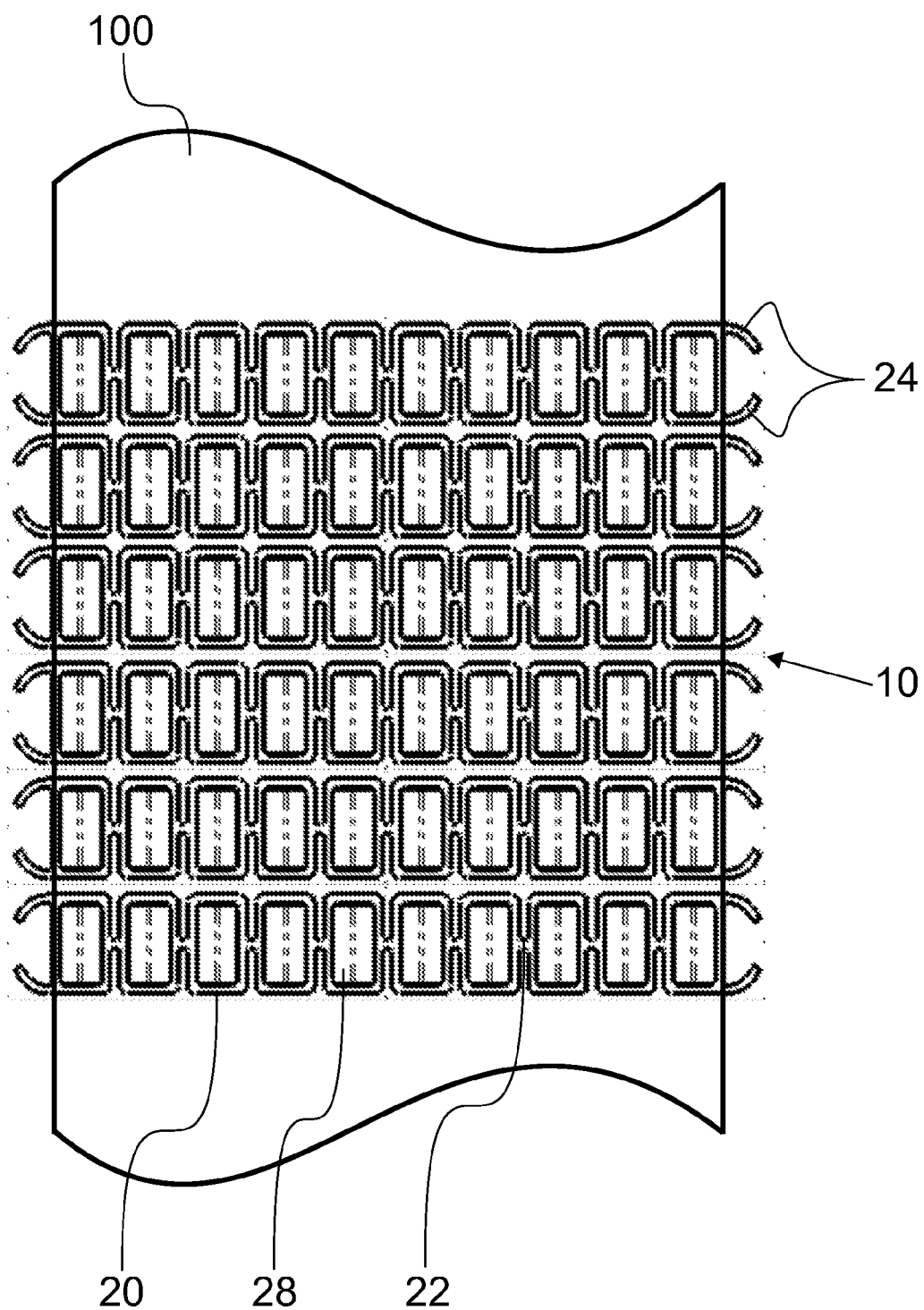
FIG. 2 illustrates one cuvette packaged in a handling package for cuvettes according the invention.

FIG. 2 shows a handling package for cuvettes according to the invention or rather a part of the package. The package comprises a row of cuvettes bound to each other by means of a bonding strip 100. In the figure, for reasons of clarity, there is a space between the cuvettes. In practice the cuvettes are touching each other in the package. The length of the row of cuvettes depends on how many cuvettes are placed in one package and the length of the row naturally also determines the length of the strip. The number of cuvettes can be e.g. 18. The size of the package is mainly determined by the number of cuvettes that can be loaded into the feed apparatus of the analyzer. The width of the bonding strip 100, on the other hand, is determined by the width of the top surface of the reaction vessels. The bonding strip must be at least wider than the space between the outermost inner walls 32 of the outermost positions 28. The maximum length is limited by the space between the tips 34 of the brackets. The greatest width of the fastening part of the bonding strip 100 must be smaller than the largest distance between the brackets 24. The fastening part of the bonding strip 100 is the part along the width of which the strip is fastened to the cuvettes. When needed, the strip can comprise protective lapels turning to the sides of the row of cuvettes and the lapels can have bonding substance on at least a portion of the area. Such lapels can, however, be disadvantageous to the handling of the package and they increase the need of the packaging material needed for the bonding strip.

The strip 100 can be, for example, a polypropylene tape having a weather-resistant, high and low temperature resistant acryl-based glue as the adhesive substance. The bonding must be strong enough to allow handling of the package, such as lifting and bending it, but on the other hand the strip must be removable by tearing without excessive force. The adhesive substance must further be non-staining and it must not leave dirt on the sides of the reaction vessels.

The adhesive substance can be e.g. an acryl dispersion glue, the adhesion strength and release strength of which are suitably chosen. The adhesive substance must have sufficient adhesive properties in both cold and heat so that the bonding is not released during storage. The bonding force of the adhesive substance must be arranged to suit the bonding area, whereby the bonding between the bonding strip and the cuvettes can be varied by changing the bonding area. The adhesive substance can be applied to a narrow area on the edges or the middle of the strip or in some other suitable way as well as, naturally, on the whole width of the strip. However, preferably there must be some adhesive substance on the location of the outermost walls of the outermost positions so that the ingress of impurities into the reaction vessels is prevented. For the same reason it is preferable that the adhesive substance be applied on the location of the outer sides of the outermost cuvettes in the ends of the package. The best closure for each reaction vessel is achieved when the adhesive substance extends to the whole bonding area, whereby the opening of each reaction vessel is closed by means of the bonding strip.

The front end of the bonding strip 100 can be provided with a bonding portion bent over the row of cuvettes during transport and storage. The bonding portion must be long enough so that it can be easily grabbed and there is no adhesive substance. The rear end of the bonding strip is preferably provided with a lapel bent to protect the optical surface of the last cuvette of the row, allowing pushing the row from behind without dirtying the optical surface of even the last cuvette. The length of the lapel is chosen so that it is slightly shorter than the height of the cuvette while still covering the optical surface. The last cuvette can this way be supported by its lower edge without disturbance by the lapel and the optical surface can be protected. The bonding portion and the lapel of the rear end does not have adhesive substance on the lower surface. The bonding strip 100 is narrower than the cuvette 10 at least such that the bonding area is narrower than the width of the cuvette so that the bonding area extends to at most to a portion of the top surface of the brackets. Most preferably the bonding area extends to the whole width of the reaction vessels, whereby the openings of the reaction vessels are surely covered. When the package is disassembled, it is possible to support the row of cuvettes from above from the upper surface of the brackets remaining free. The bonding strip 100 completely covers from above the reaction vessels of the cuvettes protecting them from dust. When the cuvettes are loaded into the instrument, the bonding strip 100 can be removed, simultaneously releasing the cuvettes from the package by supporting the package in vertical direction at the upper surfaces of the brackets. When the package is supported as described, it can be disassembled by pulling the strip off from the cuvettes, whereby they are released from the adhesive substance of the strip.

The bonding strip 100 can be made from a variety of materials and its releasable bonding can also be carried out by a number of bonding methods. Most preferably the strip is made of an elastic and resilient material, such as polypropylene or reinforced paper. Most preferably the strip is as wide as possible so that it covers the reaction vessel during transport. The strip can naturally be very narrow as well, if the protection of the reaction vessels during transport is carried out by packaging the cuvette packages into larger dust-proof delivery packages. If a wide strip is used, the adhesive substance can be applied to a portion of the width of the strip only, such as narrow areas on the edges of the strip. If the adhesive substance is applied to a narrow area only, it is possible to use glue with a good bonding capacity, while ensuring good releasability with a sufficiently small bonding area. If ultrasound welding or hot welding is used for bonding the strip, the bonding can preferably be effected by using spot-like connecting surfaces, whereby the bonding strength can be adjusted by changing the number of spots. The strip can also be made of stiff material, whereby the package becomes stiff.

In addition to the above the present invention has other embodiments as well. As has already been mentioned above, the bonding strip of the cuvettes can be made from a variety of materials and its shape can change. The strip can also be fastened to the cuvettes by using different methods. The strip can be provided with printings, such as directions of use, the name and brand of the manufacturer and information about the use and recycling the package.

The number of cuvettes in the package can vary, but using a standard package size is naturally most preferable for both the users of the instruments and the suppliers of the cuvettes. In principle it is possible to pack even a single cuvette using the inventive method, but it is economically most sensible to use the largest package size fitting an analyzer at a single loading. Thus the packaging method is the most effective and the amount of formed packaging material waste is as small as possible.

We claim:

1. A handling package of a plurality of cuvettes, the package comprising:
   a plurality of cuvettes, each of the cuvettes being formed by a plurality of reaction vessels, the reaction vessels being joined by intermediate walls between the reaction vessels, and
   a strip adhered to a surface of the reaction vessels of each of the cuvettes such that the plurality of cuvettes are arranged in a row and joined together, the strip being configured such that, upon removal of the strip, the cuvettes are no longer joined together, and wherein each of the cuvettes has a bracket at opposite ends of the cuvette,
   wherein the bracket comprises two tabs and the tabs curve toward each other.

2. The package according to claim 1, wherein the strip extends at most to an area of a top surface of openings of the reaction vessels and the bracket at the opposite ends of the cuvette extend beyond a width of the strip.

3. The package according to claim 1, wherein the strip does not extend to an area of the brackets.

4. The package according to claim 1, wherein an adhesive substance is applied only on a part of the strip.

5. The package according to claim 1, wherein the strip is attached by ultrasonic welding.

6. The package according to claim 1, wherein the strip is attached by hot welding.

7. The package according to claim 5, wherein the strip is attached by spot welding.

8. The package according to claim 2, wherein the strip does not extend to an area of the brackets.

9. The package according to claim 2, wherein an adhesive substance is applied only on a part of the width of the strip.

10. The package according to claim 1, wherein the cuvettes of the package are held parallel to each other in a row solely by an adhesive substance applied to the strip.

11. The package according to claim 2, wherein the strip is attached by ultrasonic welding.

12. The package according to claim 2, wherein the strip is attached by hot welding.

13. The package according to claim 3, wherein the strip is attached by hot welding.

14. The package according to claim 4, wherein the strip is attached by hot welding.

15. The package according to claim 5, wherein the strip is attached by hot welding.

16. The package according to claim 1, wherein the strip provides a sole means for joining the cuvettes into a handling package.

17. The package according to claim 1, wherein the intermediate wall joining the reaction vessels is narrower than the reaction vessels.

18. The package according to claim 1, wherein the strip is attached by welding.

* * * * *